(12) United States Patent
Martin et al.

(10) Patent No.: US 9,034,593 B2
(45) Date of Patent: May 19, 2015

(54) VAGINAL INDICATOR TO DETECT BIOMARKERS OF GOOD HEALTH

(75) Inventors: Stephanie M. Martin, Johns Creek, GA (US); Ronnie L. Phillips, Atlanta, GA (US); SangWook Lee, Regent Grove (SG); JunMo Gil, Daejeon (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 466 days.

(21) Appl. No.: 12/951,652

(22) Filed: Nov. 22, 2010

(65) Prior Publication Data

US 2012/0130195 A1   May 24, 2012

(51) Int. Cl.
*A61B 5/00* (2006.01)
*C12Q 1/28* (2006.01)
*C12Q 1/32* (2006.01)
*A61B 5/145* (2006.01)
(Continued)

(52) U.S. Cl.
CPC ........... *A61B 5/4337* (2013.01); *A61B 5/14507* (2013.01); *A61B 5/14546* (2013.01); *A61B 5/14735* (2013.01); *A61F 13/20* (2013.01); *C12Q 1/28* (2013.01); *C12Q 1/32* (2013.01); *A61B 2562/0295* (2013.01); *G01N 2333/90209* (2013.01); *G01N 2333/90212* (2013.01); *G01N 2333/90241* (2013.01); *G01N 2333/904* (2013.01)

(58) Field of Classification Search
CPC ............. A61B 5/14507; A61B 5/4337; A61B 5/14546; A61B 5/14735; A61B 2562/0295; C12Q 1/32; C12Q 1/28; G01N 2333/904; G01N 2333/90209; G01N 2333/90212; G01N 2333/90241

USPC ................................ 435/25, 26, 28; 600/573
See application file for complete search history.

(56) References Cited

U.S. PATENT DOCUMENTS

| | | |
|---|---|---|
| 2,912,309 A | 11/1959 | Free |
| 2,981,606 A | 4/1961 | Keston |
| 3,092,465 A | 6/1963 | Adams et al. |

(Continued)

FOREIGN PATENT DOCUMENTS

| | | | |
|---|---|---|---|
| CN | 1850985 A | * | 10/2006 |
| CN | 101324559 A | * | 12/2008 |

(Continued)

OTHER PUBLICATIONS

Garg ("Metabolic properties of lactobacilli in women experiencing recurring episodes of bacterial vaginosis with vaginal pH>5" European Journal of Clinical and Microbiology and Infectious Diseases, 2010, published online Oct. 2009, vol. 29, 123-125.*

(Continued)

*Primary Examiner* — Jon P Weber
*Assistant Examiner* — Charles Zoltan Constantine
(74) *Attorney, Agent, or Firm* — Dority & Manning, P.A.

(57) ABSTRACT

A diagnostic kit for biomarkers of beneficial vaginal health is described. The kit includes a first detection zone within which a D-lactic acid detection signal is capable of being generated, wherein the presence or quantity of D-lactic acid, is determinable from the D-lactic acid detection signal. The kit further includes a second detection zone within which a hydrogen peroxide detection signal is capable of being generated, wherein the presence or quantity of hydrogen peroxide, is determinable from the hydrogen peroxide detection signal.

12 Claims, 1 Drawing Sheet

(51) Int. Cl.
*A61B 5/1473* (2006.01)
*A61F 13/20* (2006.01)

(56) References Cited

U.S. PATENT DOCUMENTS

| | | | |
|---|---|---|---|
| 3,349,006 A | 10/1967 | Albaum | |
| 3,509,872 A | 5/1970 | Truhan | |
| 3,558,435 A | 1/1971 | Rey et al. | |
| 3,595,755 A | 7/1971 | Härtel | |
| 3,627,697 A | 12/1971 | Rey et al. | |
| 3,627,698 A | 12/1971 | Rey et al. | |
| 3,630,847 A | 12/1971 | Rey et al. | |
| 3,654,179 A | 4/1972 | Bauer | |
| 3,654,180 A | 4/1972 | Bauer | |
| 3,853,470 A | 12/1974 | Morin et al. | |
| 4,089,747 A | 5/1978 | Bruschi | |
| 4,166,763 A | 9/1979 | Esders et al. | |
| RE32,016 E | 10/1985 | Esders et al. | |
| 5,063,930 A | 11/1991 | Nucci | |
| 5,075,077 A | 12/1991 | Durley, III et al. | |
| 5,126,247 A | 6/1992 | Palmer et al. | |
| 5,217,444 A | 6/1993 | Schoenfeld | |
| 5,360,595 A | 11/1994 | Bell et al. | |
| 5,425,377 A | 6/1995 | Caillouette | |
| 5,510,244 A * | 4/1996 | Inoue et al. | 435/26 |
| 5,736,353 A | 4/1998 | Weavers et al. | |
| 5,792,618 A | 8/1998 | Starkweather et al. | |
| 5,823,953 A | 10/1998 | Raskin et al. | |
| 5,874,232 A | 2/1999 | Weavers et al. | |
| 6,093,394 A | 7/2000 | Chrisope | |
| 6,106,461 A | 8/2000 | Raskin et al. | |
| 6,372,209 B1 | 4/2002 | Chrisope | |
| 6,426,227 B1 | 7/2002 | Kritzman et al. | |
| 6,468,526 B2 | 10/2002 | Chrisope | |
| 6,472,163 B1 | 10/2002 | Coleman et al. | |
| 6,479,015 B1 * | 11/2002 | Long et al. | 422/419 |
| 6,562,297 B1 | 5/2003 | Bonstein et al. | |
| 6,607,896 B1 | 8/2003 | Millar et al. | |
| 6,627,394 B2 | 9/2003 | Kritzman et al. | |
| 6,719,691 B2 | 4/2004 | Kritzman et al. | |
| 6,921,647 B2 | 7/2005 | Kritzman et al. | |
| 6,951,759 B2 | 10/2005 | Travers et al. | |
| 7,144,709 B2 | 12/2006 | Ouyang et al. | |
| 7,314,752 B2 | 1/2008 | Kritzman et al. | |
| 7,399,608 B2 | 7/2008 | MacDonald et al. | |
| 7,521,226 B2 | 4/2009 | Song et al. | |
| 7,531,319 B2 | 5/2009 | Martin et al. | |
| 7,541,177 B2 | 6/2009 | Kritzman | |
| 7,591,978 B2 | 9/2009 | Dwir et al. | |
| 7,592,020 B2 * | 9/2009 | Boga et al. | 424/443 |
| 7,687,245 B2 | 3/2010 | Lye et al. | |
| 7,964,340 B2 | 6/2011 | Song et al. | |
| 2002/0119136 A1 | 8/2002 | Johansen | |
| 2004/0161365 A1 * | 8/2004 | Siu Yu | 422/56 |
| 2005/0131287 A1 * | 6/2005 | Kaylor et al. | 600/362 |
| 2005/0191704 A1 | 9/2005 | Boga et al. | |
| 2007/0128589 A1 * | 6/2007 | Sanders et al. | 435/5 |
| 2007/0249012 A1 | 10/2007 | Lye et al. | |
| 2008/0057528 A1 | 3/2008 | Sayre et al. | |
| 2010/0033188 A1 | 2/2010 | Reith | |
| 2010/0036212 A1 | 2/2010 | Reith | |
| 2010/0036213 A1 | 2/2010 | Reith | |
| 2010/0036214 A1 | 2/2010 | Reith | |
| 2010/0036278 A1 | 2/2010 | Reith | |
| 2010/0036279 A1 | 2/2010 | Reith | |
| 2010/0104615 A1 | 4/2010 | Jiffer | |
| 2010/0193386 A1 | 8/2010 | Loyd et al. | |
| 2010/0217101 A1 | 8/2010 | Reith | |
| 2012/0040387 A1 | 2/2012 | Matsuoka | |
| 2012/0130195 A1 | 5/2012 | Martin et al. | |

FOREIGN PATENT DOCUMENTS

| | | |
|---|---|---|
| CN | 101487041 A | 7/2009 |
| EP | 1427808 | 6/2004 |
| EP | 1481666 | 12/2004 |
| JP | 2927772 B2 | 7/1999 |
| WO | WO 00/65347 A2 | 11/2000 |
| WO | WO 00/65348 A2 | 11/2000 |
| WO | WO 2007/060649 | 5/2007 |
| WO | WO 2007/069240 | 6/2007 |
| WO | WO 2007/142609 | 12/2007 |
| WO | WO 2009/139811 A2 | 11/2009 |

OTHER PUBLICATIONS

Przybyt "Application of biosensors in early detection of contamination with lactic acid bacteria during apple juice and concentrate production" Journal of Food Engineering, 99, 2010 485-490.*

Fossati "Use of 3,5-Dichloro-2-hydroxybenzenesulfonic Acid/4-Aminophenazone Chromogenic System in Direct Enzymatic Assay of Uric Acid in Serum and Urine" Clinical Chemistry, 1980, 26 (2) 227-231.*

Montagne ("Comparison of the performance of two bi-enzymatic sensors for the detection of D-lactate" Sensors and Actuators B 26-27, (1995) 440-443).*

Feigner "Enzymatic Assay Kits for Nutrients" Sigma Aldrich, AnalytiX vol. 7 Article 4, 2011.*

American Optometric Association "The Eye and Night Vision" available at www.aoa.org/optometrists/tools-and-resources/clinical-care-publications/aviation-vision/the-eye-and-night-vision?sso=y, accessed 2014, adapted from USAF Special Report AL-SR-1992-0002, "Night Vision Manual for the Flight Surgeon" by Miller II and Tredici 1992.*

Amsel et al., "Nonspecific Vaginitis. Diagnostic Criteria and Microbial and Epidemiologic Associations", The American Journal of Medicine, vol. 74, No. 1, Jan. 1983, pp. 14-22.

Anderson et al., "Evaluation of Vaginal Complaints", Journal of the American Medical Association, vol. 291, No. 11, Mar. 2004, pp. 1368-1379.

Atassi et al., "Individual and Co-operative Roles of Lactic Acid and Hydrogen Peroxide in the Killing Activity of Enteric Strain *Lactobacillus johnsonii* NCC933 and Vaginal Strain *Lactobacillus gasseri* KS120.1 Against Enteric, Uropathogenic and Vaginosis Associated Pathogens", FEMS Microbiology Letters, vol. 304, No. 1, Mar. 2010, pp. 29-38.

Boskey et al., "Origins of Vaginal Acidity: High D/L Lactate Ratio is Consistent with Bacteria Being the Primary Source", Human Reproduction, vol. 16, No. 9, 2001, pp. 1809-1813.

Carlson et al., "Evaluation of the Oricult-N Dipslide for Laboratory Diagnosis of Vaginal Candidiasis", Journal of Clinical Microbiology, vol. 38, No. 3, Mar. 2000, pp. 1063-1065.

Cauci et al., "Prevalence of Bacterial Vaginosis and Vaginal Flora Changes in Peri- and Postmenopausal Women", Journal of Clinical Microbiology, vol. 40, No. 6, Jun. 2002, pp. 214-2152.

Cribby et al., "Vaginal Microbiota and the Use of Probiotics", Interdisciplinary Perspectives on Infectious Diseases, Nov. 2008, pp. 1-9.

Donders et al., "Wet Mount Microscopy Reflects Functional Vaginal Lactobacillary Flora Better than Gram Stain", Journal of Clinical Pathology, vol. 53, No. 4, Apr. 2000, pp. 308-314.

Hawes et al., "Hydrogen Peroxide-Producing Lactobacilli and Acquisition of Vaginal Infections", The Journal of Infectious Diseases, vol. 174, No. 5, Nov. 1996, pp. 1058-1063.

Karasz et al., "The Vaginitis Monologues: Women's Experiences of Vaginal Complaints in a Primary Care Setting", Social Science & Medicine, vol. 56, No. 5, Mar. 2003, pp. 1013-1021.

Marrazzo, "Evolving Issues in Understanding and Treating Bacterial Vaginosis", Expert Review of Anti-Infective Therapy, vol. 2, No. 6, Dec. 2004, pp. 913-922.

Mijac et al., "Hydrogen Peroxide Producing Lactobacilli in Women with Vaginal Infections", European Journal of Obstetrics and Gynecology and Reproductive biology, vol. 129,No. 1, Nov. 2006, pp. 69-76.

Rabe et al., "Optimization of Media for Detection of Hydrogen Peroxide Production by *Lactobacillus* Species", Journal of Clinical Microbiology, vol. 41, No. 7, Jul. 2002, pp. 3260-3264.

(56) References Cited

OTHER PUBLICATIONS

Schwiertz et al, "Throwing the Dice for Diagnosis of Vaginal Complaints?", Annals of Clinical Microbiology and Antimicrobials, vol. 5, No. 4, Feb. 2006, pp. 1-7.
Sobel, "Vulvovaginal Candidiasis", The Lancet, vol. 369, No. 9577, 2007, pp. 1961-1971.
Taggart, "Peroxidase Enzyme Immobilized in Nanofibers", Nov. 2009, Power Point Presentation.
Valore et al., "Reversible Deficiency of Antimicrobial Polypeptides in Bacterial Vaginosis", Infection and Immunity, vol. 74, No. 10, Oct. 2006, pp. 5693-5702.
Ferris et al., "Association of *Atopobium vaginae*, a Recently Described Metronidazole Resistant Anaerobe, with Bacterial Vaginosis", BMC Infectious Diseases, vol. 4, No. 5, Feb. 2004.
Garg et al., "Metabolic Properties of Lactobacilli in Women Experiencing Recurring Episodes of Bacterial Vaginosis with Vaginal pH≥5", European Journal of Clinical Microbiology and Infectious Diseases, Jan. 2010, vol. 29, No. 1, pp. 123-125.
Gorodeski et al., "Estrogen Acidifies Vaginal pH by Up-regulation of Proton Secretion via the Apical Membrane of Vaginal-Ectocervical Epithelial Cells", Endocrinology, vol. 146, No. 2, Feb. 2005, pp. 816-824.
Jehanno et al., "Development of a Method for Detection of Lactic Acid Bacteria Producing Exclusively the L-(+)- Isomer of Lactic Acid", Applied and Environmental Microbiology, vol. 58, No. 12, Dec. 1992, pp. 4064-4067.
Marcos et al., "Determination of D-Lactate Concentration for Rapid Diagnosis of Bacterial Infections of Body Fluids", European Journal of Clinical Microbiology & Infectious Diseases, vol. 10, No. 11, Nov. 1991, pp. 966-969.
Naglik et al., "Differential Expression of *Candida albicans* Secreted Aspartyl Proteinase and Phospholipase B Genes in Humans Correlates with Active Oral and Vaginal Infections", Journal of Infectious Diseases, vol. 188, No. 3, Aug. 2003, pp. 469-479.
Pohanka et al., "Amperometric Biosensor for D-Lactate Assay", Food Technology and Biotechnology, vol. 46, No. 1, 2008, pp. 107-110.
Shopova, "Determination of Hydrogen Peroxide Production by Vaginal Strains of *Lactobacillus* spp. Isolated from Healthy Women", Akush Ginekol (Sofiia), vol. 40, No. 3, 2001, pp. 23-24.
Smith et al., "D-Lactic Acid Measurements in the Diagnosis of Bacterial Infections", Journal of Clinical Microbiology, vol. 27, No. 3, Mar. 1989, pp. 385-388.
Sobel, "Vaginitis", New England Journal of Medicine, vol. 337, 1997, pp. 1896, 1903.
Zhou et al., "Difference in the Composition of Vaginal Microbial Communities Found in Healthy Caucasian and Black Women", International Society for Microbial Ecology, vol. 1, No. 2, Jun. 2007, pp. 121-133.
Boga et al., "Application of Visual Indicator Technology to Vaginal Odor and Potential Vaginal Infection Alert", (TR No. 2881), Oct. 31, 2003.
Hillier et al., "The Normal Vaginal Flora, H2O2-Producing Lactobacilli, and Bacterial Vaginosis in Pregnant Women", Clinic of Infectious Diseases, vol. 16, Supplemental No. 4, Jun. 1993, pp. S273-S281.
Royce et al., "Race/Ethnicity, Vaginal Flora Patterns, and pH During Pregnancy", Sexually Transmitted Diseases, vol. 26, No. 2, Feb. 1999, pp. 96-102.
Matu et al., "In Vitro Inhibitory Activity of Human Vaginal Lactobacilli Against Pathogenic Bacteria Associated with Bacterial Vaginosis in Kenyan Women", Anaerobe, vol. 16, No. 3, 2010, pp. 210-215.
Garvie "Bacterial Lactate Dehydrogenases", Microbiological Review, vol. 44, No. 1, Mar. 1980, pp. 106-139.
International Search Report and Written Opinion from PCT/IB2011/054598—7 pages, mailed Jun. 16, 2012.
Al-Mushrif et al., "A Study of the Prevalence of Hydrogen Peroxide Generating Lactobacilli in Bacterial Vaginosis: the Determination of H2O2 Concentrations Generated, in Vitro, by Isolated Strains and the Levels Found in Vaginal Secretions of Women With and Without Infection", Journal of Obstetrics and Gynecology, vol. 18, No. 1, Jan. 2000, pp. 63-67.
Falagas et al., "Probiotics for the Treatment of Women with Bacterial Vaginosis", Clinical Microbiology and Infection, vol. 13, No. 7, Jul. 2007, pp. 657-664.

* cited by examiner

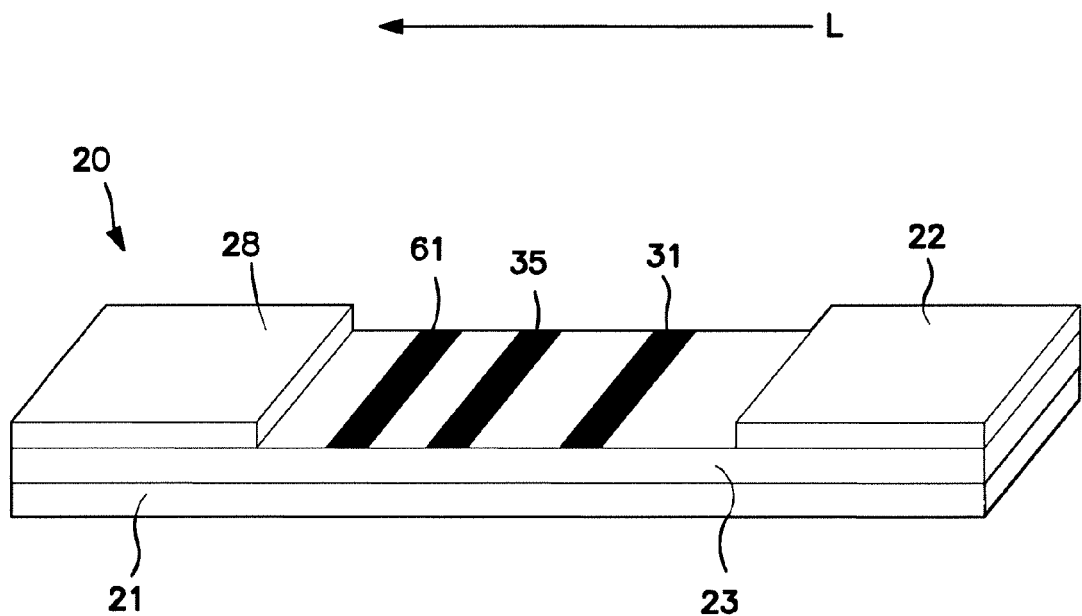

VAGINAL INDICATOR TO DETECT BIOMARKERS OF GOOD HEALTH

BACKGROUND

The female vagina is naturally colonized by a variety of bacteria, yeast, and microorganisms. For example, a normal vagina generally contains more than about $10^4$ lactobacilli per milliliter of vaginal fluid. Under normal conditions, the vagina flora provides a mildly acidic environment that helps guard against the invasion of pathogenic microbes. Unfortunately, this vaginal balance may be easily upset by a variety of external factors that ultimately lead to vaginal infection.

Bacterial vaginosis, for example, is a polymicrobial vaginal infection believed to be caused by an increase in the number of anaerobic organisms with a concomitant decrease in lactobacilli in the vagina. The decrease in the number of lactobacilli in the vagina has the dual effect of decreasing competition for nutrients and decreasing the amount of lactic acid present (i.e., increasing the pH). This allows for the multiplication of opportunistic pathogens in the vagina, whose growth is normally suppressed by the lactobacilli and the acidic pH of the vagina. *Atopobium vaginae, Bacteroides* spp., *Gardnerella vaginalis, Mobiluncus, Megasphera, Mycoplasma hominis, Peptostreptococcus*, and *Prevotella* are some of the species that are prevalent during a BV infection.

Symptoms of bacterial vaginosis generally include an unpleasant smell, an elevated vaginal pH greater than about 5.0, a thin homogeneous discharge, and the presence of clue cells (i.e., vaginal epithelial cells coated with small Gram-variable rods).

Current treatment regimens for bacterial infection of the vagina involve the use of various broad spectrum antibiotics, such as metronidazole. However, antibiotics are often undesirable because they may kill a broad range of the normal bacterial flora in the vagina, including the beneficial lactobacilli. This may cause secondary complications, because the lactobacilli keep various opportunistic pathogens in the vagina in check. The treatment may then necessitate a further treatment regimen, such as the ingestion of cultured dairy products to replace the lactobacilli in the body, as well as treatment by antifungal agents. A rise in the level of anaerobes due to a lack of lactobacilli could further complicate the infection. Antibiotics, when used frequently within the vagina, may cause systemic toxicity through absorption from the vagina. Moreover, the relative ease of treatment should not be misinterpreted as having no clinical implications. Pregnancy, in particular, is a time where bacterial vaginosis can cause serious problems. Bacterial vaginosis is becoming more recognized as a contributing factor in preterm delivery, and increased morbidity and mortality during birth.

Previous efforts at tests for bacterial vaginosis have been limited to detection of biomarkers associated specifically with infection. The obvious drawback of such approaches is that a bacterial vaginosis infection must already be present for the test to detect the same. Heretofore, no test exists that can provide frequent assessment of vaginal health so as promote better hygiene behaviors and possibly alter behavior to avoid bacterial vaginosis infection as well as other infections. Specifically, no test exists in which women can be provided significant reassurance when healthy and guidance for proper vaginal care when not.

As such, a need currently exists for fast, inexpensive, and easy to use tests which are capable of informing women about their vaginal health. Methods of utilizing such tests would also be beneficial.

SUMMARY

In accordance with one embodiment of the present invention, a diagnostic kit for biomarkers of beneficial vaginal health is described. The kit includes a first detection zone within which a D-lactic acid detection signal is capable of being generated, wherein the presence or quantity of D-lactic acid, is determinable from the D-lactic acid detection signal. The kit further includes a second detection zone within which a hydrogen peroxide detection signal is capable of being generated, wherein the presence or quantity of hydrogen peroxide, is determinable from the hydrogen peroxide detection signal.

In yet another embodiment of the present disclosure, a method for detecting biomarkers of beneficial vaginal health is described. The method includes contacting a test sample with a test kit comprising a first detection zone within which a D-lactic acid detection signal is capable of being generated. The presence or quantity of D-lactic acid, is determinable from the D-lactic acid detection signal. The test kit further comprises a second detection zone within which a hydrogen peroxide detection signal is capable of being generated, wherein the presence or quantity of hydrogen peroxide is determinable from the hydrogen peroxide detection signal. The method further includes detecting the presence or quantity of D-lactic acid from the D-lactic acid detection signal and determining the presence or quantity of hydrogen peroxide from the hydrogen peroxide detection signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 1 is a perspective view of one embodiment of an assay device that may be used in the diagnostic test kit of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "vagina" generally refers to the internal structure of the female reproductive tract extending from the cervix of the uterus to the vestibule. The term is also intended to include the external genitalia (e.g., labia majora, labia minora, and clitoris).

As used herein, the term "test sample" generally refers to a material that is tested for certain biomarkers which can be indicative of the state of vaginal health. For example, the test sample may be obtained or derived from a biological source, such as a physiological fluid. In addition, a solid material may be used as the test sample. The test sample may be used directly as obtained from a source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, etc. Moreover, it may also be beneficial to modify a solid test sample to form a liquid medium.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a technique for detecting the presence and/or quantity of biomarkers that are indicative of the state of vaginal health. For example, in certain embodiments, a diagnostic test kit is employed that can be used to indicate the presence and/or quantity of lactic acid and hydrogen peroxide, respectively, within a test sample.

In this regard, the vagina and lactobacilli form a symbiotic relationship where the vaginal epithelium cells provide nutrients in the form of glycogen, which maintains the *lactobacillus* population, and the *lactobacillus* flora provides defense against other pathogens. Specifically, lactobacilli produce lactic acid (also referred to herein interchangeably as lactate), which acidifies the vagina, and hydrogen peroxide (also referred to herein interchangeably as peroxide), which prevents overgrowth of pathogens. Both lactic acid and hydrogen peroxide are produced in copious amounts by the *lactobacillus* population of a healthy vagina.

Lactic acid has two isomeric forms, L-lactic acid and D-lactic acid. L-lactic acid is produced by both the human body and bacteria, while D-lactic acid is produced only by bacteria. In the vaginal flora, *lactobacillus* is known to be the only bacterial species that produce D-lactic acid in significant quantity. Although vaginal epithelial cells produce some D-lactic acid, it is believed that most of the vaginal D-lactic acid is produced by the *lactobacillus* flora. Therefore, the quantity of D-lactic acid is an accurate indication of the state of vaginal health. It has been determined that the presence of D-lactic acid in the vagina in amounts greater than about 10 mg/mL of a test sample indicates a healthy state. For instance, in certain embodiments, the presence of D-lactic acid in the vagina in amounts greater than about 12 mg/mL indicates a healthy state. In certain embodiments, the presence of D-lactic acid in the vagina in amounts greater than about 15 mg/mL indicates a healthy state and in still other embodiments, the presence of D-lactic acid in the vagina in amounts greater than about 20 mg/mL, 50 mg/mL, 100 mg/mL, or 200 mg/mL indicates a healthy state.

Detection of D-lactic acid can be accomplished by an enzyme-based assay such as an assay utilizing D-lactate dehydrogenase or D-lactate oxidase. D-lactate dehydrogenase creates the reduced form of nicotinamide-adenine dinucleotide (NADH) while D-lactate oxidase creates hydrogen peroxide.

For instance, in certain embodiments, the quantification of D-lactic acid can include multiple enzyme reactions. In the first reaction catalyzed by D-lactate dehydrogenase (D-LDH), D-lactic acid (D-lactate) is oxidized to pyruvate in the presence of nicotinamide-adenine dinucleotide (NAD+) (1).

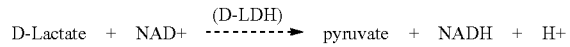

(1)

However, since the equilibrium of reaction (1) favors D-lactic acid and NAD+, a further reaction can be utilized to "trap" the pyruvate product. This is achieved by the conversion of pyruvate to D-alanine and 2-oxoglutarate, with the enzyme D-glutamate-pyruvate transaminase (D-GPT) in the presence of a large excess of D-glutamate (2).

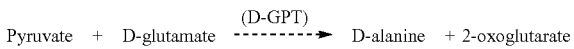

(2)

The amount of NADH formed in (1) above is stoichiometric with the amount of D-lactic acid. A suitable color agent in the presence of diaphorase can be utilized to quantify the amount of D-lactic acid present in the test sample (3).

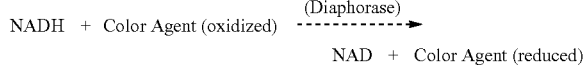

(3)

Suitable color agents can include tetrazolium reagents including the following: pABT (p-Anisyl Blue Tetrazolium Chloride); pApNBT, p-Anisyl-p-Nitro Blue Tetrazolium Chloride; BSPT, Thiazolyl blue (2-2'-Benzothiazolyl-5-styryl-3-(4'-phthalhydrazidyl)tetrazolium chloride); B T, Blue tetrazolium chloride; BTSPT, 2-(2'-Benzothiazolyl)-5-styryl-3-(4'-phthalhydrazidyl)-tetrazolium chloride; CTC, (5-Cyano-2,3-ditolyltetrazolium chloride); DMDPT, [3-(4,5-Dimethylthiazol-2-yl)-2,5-diphenyl]tetrazolium Bromide, 1-[4,5-dimethylthiazol-2-yl]-2,5-diphenyltetrazolium bromide; DSNBT, Distyryl nitroblue tetrazolium chloride; (1H)-tetrazole; IDNTT, Iodonitrotetrazolium chloride; INT, Iodo Nitro Tetrazolium Violet Chloride, p-iodo nitrotetrazolium violet (2-(4-iodophenyl)-3-(4-nitrophenyl)-5-phenyltetrazolium chloride; INpT, 2-(p-iodophenyl)-p-nitrophenyl-5-phenyltetrazolium chloride; mNBT, m-Nitro Blue Tetrazolium Chloride; mNNT, m-Nitro Neotetrazolium Chloride; MNSTC, 2,2-bis(2-methoxyl-4-nitro-5-sulfophenyl)-2H-tetrazolium-5-carboxanilide; MTS: 3-(4,5-dimethylthiazol-2-yl)-5-(3-carboxymethoxyphenyl)-2-(4-sulfophenyl)-2H-tetrazolium salt; MTT, tetrazolium bromide, thiazolyl blue tetrazolium bromide, (3->4,5-dimethylthiazol-2-yl!-2,5-diphenyltetrazolium bromide); NBMT, Nitro Blue Monotetrazolium Chloride; NBT, p-Nitro Blue Tetrazolium Chloride, Nitro blue tetrazolium chloride (2,2'-di-nitrophenyl-5,5'-diphenyl-3,3'-(3,3'-dimethoxy-4,4'-diphenylene)-ditetrazolium chloride); NT, Neotetrazolium chloride (2,2',5,5'-Tetraphenyl-3,3'(p-diphenylene)-ditetrazolium chloride; NTV, Nitrotetrazolium Violet; Thiazolyl blue; TB, tetrazolium blue chloride (3,3'->3,3'-dimethoxy(1,1'-biphenyl)-4,4'-diyl]-bis (2,5-diphenyl-2H-tetrazolium)dichloride); NBT, Nitroblue tetrazolium chloride; oTTR, o-Tolyl Tetrazolium Red; PCTMB, sodium 3'-[1-[(phenylamino)-carbonyl]-3,4-tetrazolium]-bis(4-methoxy-6-nitro)ben-zene-sulfonic acid hydrate; PNBT, p-Nitro Blue Tetrazolium Chloride; PTB, Piperonyl Tetrazolium Blue; pTTR, p-Tolyl Tetrazolium Red; TC-NBT, Thiocarbamyl nitro blue tetrazolium chloride (2,2'-di-p-nitrophenyl-5,5'-di-p-thiocarbamylphenyl-3,3'[3,3'-dimethoxy-4-,4'-biphenylene]-ditetrazolium chloride; TNBT, Tetranitroblue tetrazolium chloride; TPTT, 1,3,5-triphenyltetrazolium; TR, TTC, TPT, Tetrazolium Red (2,3,5-triphenyltetrazolium chloride); TV, Tetrazolium violet, Violet Tetrazolium, 2,3,5-Triphenyl-2-H-tetrazolium chloride, 2,5-diphenyl-3-[.alpha.-naphthyl]-tetrazolium chloride, 2,5-diphenyl-3-[1-naphthyl]-2H-tetrazolium chloride; VTB, Veratryl tetrazolium blue; WST-1: 4-[3-(4-iodophenyl)-2-(4-nitrophenyl)-2H-5-tetrazolio]-1,3-benzene disulfonate; XTT, 2,2-bis(2-methoxyl-4-notro-5-sulfophenyl)-2H-tetrazolium-5-carboxanilide, as well as other color agents as would be known in the art.

The level of D-Lactic acid present in the test sample can be determined in mg/mL by comparing the developed color to a color chart which can be provided with the diagnostic test kit of the present disclosure. If test sample color falls between two color chips, an intermediate value for the test sample D-lactic acid level can be selected.

As described above, lactate oxidase is also capable of catalyzing the conversion of D-lactic acid to pyruvate and hydrogen peroxide in the presence of oxygen to quantitatively determine the level of D-lactic acid in a test sample. Various lactate oxidases as would be known in the art can be utilized for such purpose. One such lactate oxidase which can convert D-lactic acid to pyruvate and hydrogen peroxide is produced by Streptococcus faecalis ATCC 12755.

When a test sample containing an unknown quantity of D-lactic acid is assayed using lactate oxidase, hydrogen peroxide is produced in proportion to the quantity of D-lactic acid in the test sample. The hydrogen peroxide can be detected by any known method and the unknown quantity of D-lactic acid can be determined.

Known methods for detecting and/or quantifying hydrogen peroxide in assays generally use a composition containing a substance having peroxidative activity, e.g., peroxidase and peroxidase-like substances, and material which undergoes a detectable change (generally a visible change) in the presence of hydrogen peroxide and the peroxidative substance. In the presence of hydrogen peroxide, the combination of peroxidase or peroxidase-like substances and a compatible material which causes color change (such as a redox dye) creates a color whose intensity can be proportional to the concentration of hydrogen peroxide, and thereby the concentration of D-lactic acid. The D-Lactic acid level of the test sample can be determined in mg/mL by comparing the developed color to a color chart which can be provided with the diagnostic test kit of the present disclosure.

Representative patents which describe materials which can be used in connection with hydrogen peroxide include: U.S. Pat. Nos. 2,912,309; 2,981,606; 3,349,006; 3,092,465; 3,558,435; 3,595,755; 3,627,697; 3,627,698; 3,630,847; 3,654,179; 3,654,180; and 3,853,470, which are incorporated by reference herein. Examples of various color forming substrates of peroxidase and peroxidase-like substances which have been suggested in the prior art include, among others, the following substances with a coupler where necessary:

(1) Monoamines, such as aniline and its derivatives ortho-toluidine, para-toluidine, and the like;
(2) Diamines, such as ortho-phenylenediamine, N,N'-dimethyl-para-phenylenediamine, N,N'-diethyl phenylenediamine, benzidine (which produces a blue or brown color), dianisidine (turns green or brown), and the like;
(3) Phenols, such as phenol (producing a yellow color), thymol, ortho-, meta-, and para-cresols (producing a green-yellow color, a pink color and a milky suspension, respectively), alpha-naphthol (producing a magenta color), beta-naphthol (producing a white precipitate), and the like;
(4) Polyphenols, such as catechol, guaiacol (which forms an orange color), orcinol, pyrogallol (producing a reddish or yellow color), p,p-dihydroxydiphenyl and phloroglycinol;
(5) Aromatic acids, such as salicylic, pyrocatechuic and gallic acids;
(6) Leuco dyes, such as leucomalachite green (to produce malachite green), tetramethylbenzidine (TMB), and leucophenolphthalein (desirably employed in an alkaline medium);
(7) Colored dyes, such as 2,6-dichlorophenolindophenol;
(8) Various biological substances, such as epinephrine, the flavones, tyrosine, dihydroxyphenylalanine (producing an orange-reddish color) and tryptophan;
(9) Other substances, such as ammonium molybdate, gum guaiac, guaiaconic acid, potassium, starch, potassium iodide, sodium (such as N-(carboxymethylaminocarbonyl)-4,4-bis(dimethylamino)-diphenylamine sodium salt), and other water soluble iodides; and bilirubin (producing a greenish color); and
(10) Such particular dyes as 2,2'-azino-bis(3-ethylbenzthiazoline-6-sulphonic acid) and 3,3'-diaminobenzidine.

A peroxidase is an enzyme which will catalyze a reaction wherein hydrogen peroxide oxidizes another substance. The peroxidases are generally conjugated proteins containing iron porphyrin. Peroxidase occurs in horseradish, potatoes, fig tree sap and turnips (plant peroxidase); in milk (lacto peroxidase); and in white blood corpuscles (verdo peroxidase); also it occurs in microorganisms and may be produced by fermentation. Certain synthetic peroxidases are also satisfactory for use in hydrogen peroxide detection systems. Also satisfactory are such substances as hemin, methemoglobin, oxyhemoglobin, hemoglobin, hemochromogen, alkaline hematin, hemin derivatives and certain other compounds which demonstrate peroxidative or peroxidase-like activity, namely, the ability to catalyze the oxidation of another substance by means of hydrogen peroxide and other peroxides.

Other substances which are not enzymes but which demonstrate peroxidative activity are: iron sulfocyanate, iron tannate, ferrous ferrocyanide, chromic salts (such as potassium chromic sulfate) absorbed in silica gel, and the like.

Referring again to the biomarkers indicative of good vaginal health, another biomarker that will be considered in accordance with the present disclosure is hydrogen peroxide. Lactobacilli are responsible for the production of microbiocidal compounds in the vagina such as lactic acid, bacteriocines, and hydrogen peroxide. The latter is believed to play an especially important role in preventing overgrowth of pathogens in the vagina. *Lactobacillus* utilizes flavoproteins which convert oxygen to hydrogen peroxide. Hydrogen peroxide can inhibit bacteria, fungi, viruses, and mammalian cells because many bacteria lack an enzyme called catalase that breaks down hydrogen peroxide and protect them from oxidation by hydrogen peroxide. Alone or combined with halide and peroxidases present in vaginal secretions, hydrogen peroxide also displays toxic properties as evidenced by in vitro studies showing killing of HIV 1, *Gardnerella vaginalis, Bacterioides* sp., *Neisseria gonohorreae*, and *Candida albicans*.

It is believed that women with bacterial vaginosis have a significantly lower concentration of peroxide in the vagina. As such, the level of hydrogen peroxide can be used as a health state indicator as well. In addition, presence of *Mobi-*

*liuncus* species and *G. vaginalis*, coupled with low concentrations of peroxide-producing *Lactobacillus* species have been linked to preterm delivery among pregnant women with bacterial vaginosis. It has been determined that the presence of hydrogen peroxide in the vagina in amounts greater than about 1 micromoles per liter of a test sample indicates a healthy state. For instance, in certain embodiments, the presence of hydrogen peroxide in the vagina in amounts greater than about 5 micromoles per liter indicates a healthy state. In certain embodiments, the presence of hydrogen peroxide in the vagina in amounts greater than about 10 micromoles per liter indicates a healthy state and in still other embodiments, the presence of hydrogen peroxide in the vagina in amounts greater than about 15 micromoles per liter, 20 micromoles per liter, 50 micromoles per liter or 100 micromoles per liter indicates a healthy state.

Known methods for detecting and/or quantifying hydrogen peroxide in assays are described above in relation to when D-lactic acid is assayed using lactate oxidase, hydrogen peroxide is produced in proportion to the quantity of D-lactic acid in the test sample. Other suitable methods for detecting and/or quantifying the hydrogen peroxide present in the test sample can also be utilized.

For example, the diagnostic kit of the present disclosure can employ a chromogen that is capable of undergoing a detectable color change in the presence of hydrogen peroxide. Without intending to be limited by theory, it is believed that oxidation of the chromogen induces either a shift of the absorption maxima towards the red end of the spectrum ("bathochromic shift") or towards the blue end of the spectrum ("hypsochromic shift"). The absorption shift provides a color difference that is detectable, either visually or through instrumentation, to indicate the presence of hydrogen peroxide within the test sample. For example, prior to contact with a test sample, the chromogen may be colorless or it may possess a certain color. However, after contacting the test sample and reacting with hydrogen peroxide, the chromogen exhibits a color that is different than its initial color. The color change may thus be readily correlated to the presence of the hydrogen peroxide in the test sample.

The chromogen can be a leuco base, or a derivative thereof, which is capable of exhibiting a detectable change in color upon oxidation. For example, arylmethane leuco bases (e.g., diarylmethanes and triarylmethanes) are particularly suitable oxidizable chromogens for use in the present disclosure. Triarylmethane leuco bases, for example, have the following general structure:

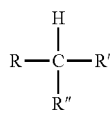

wherein R, R', and R" are independently selected from substituted and unsubstituted aryl groups, such as phenyl, naphthyl, anthracenyl, etc. The aryl groups may be substituted with functional groups, such as amino, hydroxyl, carbonyl, carboxyl, sulfonic, alkyl, and/or other known functional groups. Examples of such triarylmethane leuco bases include leucomalachite green, pararosaniline base, crystal violet lactone, crystal violet leuco, crystal violet, CI Basic Violet 1, CI Basic Violet 2, CI Basic Blue, CI Victoria Blue, N-benzoyl leuco-methylene, etc. Likewise suitable diarylmethane leuco bases may include 4,4'-bis (dimethylamino) benzhydrol (also known as "Michler's hydrol"), Michler's hydrol leucobenzotriazole, Michler's hydrol leucomorpholine, Michler's hydrol leucobenzenesulfonamide, etc. In addition to arylmethane leuco bases, other chromogens that may exhibit a detectable color change in the presence of hydrogen peroxide are described in U.S. Pat. No. 4,089,747 to Bruschi, which is incorporated herein in its entirety by reference thereto for all purposes.

In one particular embodiment, the chromogen is leucomalachite green (or an analog thereof), which is generally colorless and has the following structure:

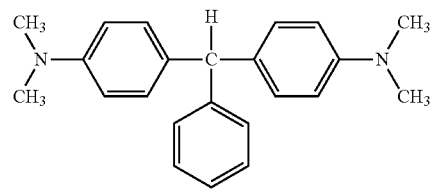

Upon oxidation with hydrogen peroxide, leucomalachite green forms malachite green carbinol (Solvent Green 1), which has the following structure:

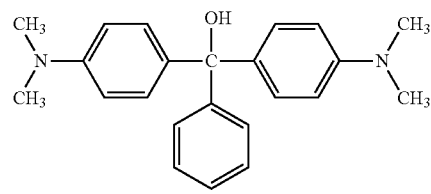

The carbinol form of leucomalachite green is also colorless. However, under acidic conditions, one or more free amino groups of the leucomalachite green carbinol form may be protonated to form malachite green (also known as aniline green, basic green 4, diamond green B, or victoria green B), which is green in color and has the following structure:

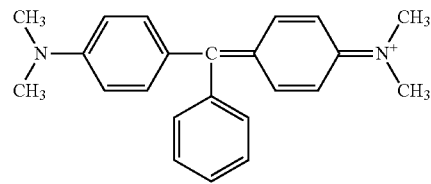

The hydrogen peroxide released by the enzyme-catalyzed oxidation of the analyte may directly induce a color change in the chromogen as described above. Because hydrogen peroxide has a relatively low oxidation potential for certain chromogens, however, it is sometimes difficult to detect the color change (e.g., visibly) when the peroxide is released in low concentrations (e.g., less than 5 wt. % of the test sample). In this regard, an electron donor may optionally be employed to react with hydrogen peroxide and produce an intermediate compound having a higher oxidation potential for the chromogen than hydrogen peroxide. A variety of known electron donors may be employed for this purpose. In one embodiment, for example, an excess amount of iodide ions ($I^-$) in aqueous solution may react with hydrogen peroxide to form triiodide ions ($I_3^-$), which have a much greater oxidation potential than hydrogen peroxide. Exemplary sources of ionic iodide include hydrogen iodide (HI) and water-soluble iodide salts, such as alkali metal iodide salts (e.g., potassium iodide (KI), sodium iodide (NaI), lithium iodide), ammonium iodide ($NH_4I$), calcium iodide ($CaI_2$), etc.). Other suitable electron donors may include a source of thiocyanate ions, such as sodium thiocyanate, potassium thiocyanate, ammonium thiocyanate, and other thiocyanate salts. Metals, such as iron(II), may also be used as electron donors. For example, Fenton's reagent is a solution that is formed by reaction of iron(II) and hydrogen peroxide. That is, iron(II) is oxidized to iron(III) by hydrogen peroxide to form a hydroxyl radical and a hydroxyl anion. Iron(III) is then reduced back to iron(II) by the same hydrogen peroxide to a peroxide radical and a proton. The resulting reagent has a strong oxidation potential for the chromogen. Still other suitable electron donors are described in U.S. Patent Application Publication No. 2002/0119136 to Johansen, which is incorporated herein in its entirety by reference thereto for all purposes.

Although the electron donor may provide intermediate compounds with a high oxidation potential, the concentration of such compounds may nevertheless be too low in some cases to produce the desired color change in the chromogen. For example, high concentrations of a triiodide ion may result in a color (e.g., golden brown) that is visible to the human eye. However, as its concentration decreases, the color becomes less apparent. Thus, a color developer may be employed that complexes to the intermediate compound (e.g., triiodide ions) to form a more intense color. One particular example of such a color developer is starch, which encompasses both natural starch and modified derivatives, such as dextrinated, hydrolyzed, alkylated, hydroxyalkylated, acetylated or fractionated starch. Starches are generally formed from two structurally distinctive polysaccharides, i.e., .alpha.-amylose and amylopectin, both of which are comprised of .alpha.-D-glucopyranose units. The starches may be of or derived from any origin, such as corn starch, wheat starch, potato starch, tapioca starch, sago starch, rice starch, waxy corn starch or high amylose corn starch. When employed in conjunction with an iodide source, such as described above, the a-amylose portion of the starch may entrap or bind to the triiodide ion to form a linear triiodide ion complex that is water-soluble and has an intense blue color.

The extent to which the electron donor and/or color developer facilitate the desired color change depends in part on their concentration. That is, too large of a concentration of one or more of these components may overwhelm the chromogen and stifle the oxidation reaction. On the other hand, too low of a concentration may not enhance the oxidation potential to the desired extent. In this regard, the electron donor (e.g., iodide source) may be employed in an amount from about 0.01 to about 2000 millimoles ("mM"), in some embodiments from about 0.1 to about 1000 mM, and in some embodiments, from about 1 to about 100 mM per liter of the test sample. The color developer (e.g., starch) may likewise be employed in an amount from about 0.001 to about 10 wt. %, in some embodiments from about 0.01 to about 5 wt. %, and in some embodiments, from about 0.1 to about 2 wt. % based on the weight of the test sample.

To achieve the desired color change in accordance with the present disclosure, the chromogen is applied to a reaction medium in a manner so that it does not substantially diffuse through the matrix of the medium (i.e., non-diffusively immobilized). This enables a user to readily detect the change in color that occurs upon oxidation of the chromogen. For example, a solution containing the chromogen may be initially applied to the reaction medium within a detection zone. The chromogenic solution may contain an aqueous and/or non-aqueous solvent depending on the material used to form the chromatographic medium. Suitable non-aqueous solvents may include glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone; triacetin; acetonitrile, tetrahydrafuran; xylenes; formaldehydes (e.g., dimethylformamide); etc. The amount of the solvent and chromogen in the solution may generally vary based on the desired level of sensitivity. For instance, in some embodiments, the chromogen may be present at a concentration from about 0.1 to about 100 milligrams per milliliter of solvent, in some embodiments from about 0.5 to about 60 milligrams per milliliter of solvent, and in some embodiments, from about 1 to about 40 milligrams per milliliter of solvent.

Regardless, the solution may be dried to remove the solvent and leave a residue of the chromogen on the medium. The chromogen will generally remain within the detection zone until contacted with the fluidic test sample. Because the chromogen is water-soluble, however, it would normally dissolve and flow with the test sample unless otherwise immobilized. Thus, in accordance with the present invention, the chromogen is substantially non-diffusively immobilized within the detection zone in conjunction with an anionic compound, i.e., a compound that contains one or more anions or is capable of forming one or more ions in solution. Such anionic compounds may facilitate immobilization of the chromogen in a variety of ways. For example, anionic compounds may also enhance the charge of the chromogen so that forms an ionic bond with one or more functional groups present on the surface of the chromatographic medium. In addition, certain anionic compounds (e.g., acids) may form a substantially water-insoluble precipitate when reacted with a leuco base or derivative thereof (e.g., protonated leuco base). Of course, the anionic compound may also provide a variety of other benefits. For example, a small amount of the chromogen may undergo an oxidation reaction if left in air or other oxidizing environment for too great a period of time. This may lead to a change in color that would adversely affect the ability to semi-quantitatively or quantitatively determine the presence of the hydrogen peroxide. The anionic compound may help protect the chromogen from inadvertent oxidation.

The selection of the anionic compound depends on a variety of factors, including the nature of the chromogen and its concentration. Suitable anionic compounds for use in the present disclosure may include, for instance, inorganic acids, such as hydrochloric acid, nitric acid, sulfuric acid, phosphoric acid, polyphophoric acid, boric acid, boronic acid, etc.; organic acids, including carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid, citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; sulfonic acids, such as methanesulfonic acid, benzenesulfonic acid, toluenesulfonic acid, trifluoromethanesulfonic acid, styrenesulfonic acid, naphthalene disulfonic acid, hydroxybenzenesulfonic acid, etc.; polymeric acids, such as poly(acrylic) or poly(methacrylic) acid and copolymers thereof (e.g., maleic-acrylic, sulfonic-acrylic, and styrene-acrylic copolymers), carageenic acid, carboxymethyl cellulose, alginic acid, etc.; and so forth. Anhydrides (e.g., maleic anhydride) and salts of the aforementioned acids may also be employed. The salts may be in the form of metal salts, such as sodium salts, potassium salts, calcium salts, cesium salts, zinc salts, copper salts, iron salts, aluminum salts, zirconium salts, lanthanum salts, yttrium salts, magnesium salts, strontium salts, cerium salts), or salts prepared by reacting the acids with amines (e.g., ammonia, triethylamine, tributyl amine, piperazine, 2-methylpiperazine, polyallylamine).

The degree to which the chromogen is immobilized may depend on the concentration of the anionic compound. For instance, the concentration of the anionic compound in the chromogenic solution may be from about 0.1 to about 20 millimoles per liter ("mM"), in some embodiments from about 1 mM to about 10 mM, and in some embodiments, from about 2 mM to about 8 mM.

In accordance with the present disclosure, the desired reaction time between the reagents (e.g., enzyme, hydrogen peroxide, electron donor, color developer, etc.) may be achieved by selectively controlling the medium in which the reactions occur. That is, the reaction medium is chromatographic in nature so that the hydrogen peroxide and/or other reagents are allowed to flow laterally in a consistent and controllable manner. While laterally flowing through the medium, the hydrogen peroxide oxidizes the chromogen, which is contained within a discrete detection zone for analysis. Due to the nature of the controlled fluid flow, any unreacted reagents travel to the end of the reaction medium so that it is unable to adversely interfere with observance of the chromogen within the detection zone.

Referring to FIG. 1, for instance, one embodiment of an assay device 20 that may be used in the present invention will now be described in more detail. As shown, the assay device 20 contains a chromatographic medium 23 optionally carried by a support 21. The chromatographic medium 23 may be made from any of a variety of materials through which a fluid is capable of passing, such as a fluidic channel, porous membrane, etc. For example, the chromatographic medium 23 may be a porous membrane formed from materials such as, but not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The support 21 may be formed from any material able to carry the chromatographic medium 23. Although not required, the support 21 may be transparent so that light readily passes therethrough. In addition, it is also generally desired that the support 21 is liquid-impermeable so that fluid flowing through the medium does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. As is well known the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate structures are described in U.S. Pat. No. 5,075,077 to Durley, III., et al., which is incorporated herein in its entirety by reference thereto for all purposes.

The assay device 20 may also contain an absorbent material 28. The absorbent material 28 generally receives fluid that has migrated through the entire chromatographic medium 23. As is well known in the art, the absorbent material 28 may assist in promoting capillary action and fluid flow through the medium 23.

The assay device 20 may also include a sample pad 22 or other material that is in fluid communication with the chromatographic medium 23. Some suitable materials that may be used to form the sample pad 22 include, but are not limited to, nitrocellulose, cellulose, porous polyethylene pads, and glass fiber filter paper. If desired, the sample pad 22 may contain one or more assay pretreatment reagents, either diffusively or non-diffusively attached thereto.

Generally speaking, the manner in which the assay device 20 functions may depend on the type of species selected for the reactive complexes. In this regard, various techniques for using the assay device 20 will now be described in more detail. For example, as stated above, the reactive complexes are generally allowed to incubate with the test sample for a certain period of time. This incubation process may be conducted before applying the test sample to the chromatographic medium 23, or it may be incorporated as part of the assaying procedure (i.e., incubation occurs after the test sample is applied, such as within an incubation well). For instance, the incubation mixture may be directly applied to a portion of the chromatographic medium 23 through which it may then travel in the direction illustrated by arrow "L" in FIG. 1. Alternatively, the mixture may first be applied to the sample pad 22.

Regardless, the chromatographic medium 23 defines a first detection zone 31 within which the presence and quantity of D-lactic acid can be determined. The first detection zone 31 may generally provide any number of distinct detection regions so that a user may better determine the concentration of D-lactic acid within a test sample. Each region may contain the same or different receptive materials. For example, the first detection zone 31 may include two or more distinct detection regions (e.g., lines, dots, etc.). The use of two or more distinct detection regions may provide certain benefits, such as facilitating semi-quantitation. The detection regions may be disposed in the form of lines in a direction substantially perpendicular to the flow of the test sample through the chromatographic medium 23. Likewise, in some embodiments, the detection regions may be disposed in the form of lines in a direction substantially parallel to the flow of the test sample through the medium 23. It should be understood that one or more distinct regions of the first detection zone 31 may exhibit the above-described relationship between signal intensity and D-lactic acid concentration; however, each distinct region need not exhibit such a relationship.

Within the second detection zone 35, the presence and quantity of hydrogen peroxide can be determined. The second detection zone 35 can be similar to the first detection zone 31 except for the ability to detect hydrogen peroxide. However, as discussed above, detection of D-lactic acid in the first detection zone 31 can be accomplished by an assay utilizing D-lactate oxidase, which also creates hydrogen peroxide. In such embodiments, the detection zones can be kept separate so as to allow for accurate calculation of the respective biomarkers.

A still third detection zone 61 can be present which can serve as a control, if desired, for one or more of the previous zones and biomarkers being tested.

After the assaying procedure, the first detection zone 31 and the second detection zone 35 may be analyzed, either qualitatively (e.g., visual observation), or semi-quantitatively or quantitatively (e.g., using instrumentation), for the presence or intensity of a respective signal. Depending on the nature of the reporters and the chemichromic dye utilized, the same or different detection techniques may be employed for the first detection zone 31 as the second detection zone 35.

In certain embodiments, the detection zones of the present device have a sensitivity which allows detection of relatively small concentrations of the biomarkers being detected. For instance, in certain embodiments, the first detection zone 31 is configured to have a sensitivity such that it is capable of detecting at least about 1 millimoles per liter of D-lactic acid. In still other embodiments, the first detection zone 31 is configured to have a sensitivity such that it is capable of detecting at least about 5 millimoles per liter of D-lactic acid, and in still other embodiments, 10 millimoles per liter of D-lactic acid. In certain embodiments, the first detection zone 31 is configured to have a sensitivity such that it is capable of detecting from at least about 1 millimole per liter to at least about 100 millimoles per liter of D-lactic acid.

Similarly, in certain embodiments, the second detection zone 35 is configured to have a sensitivity such that it is capable of detecting at least about 0.5 micromoles per liter of hydrogen peroxide. In still other embodiments, the second detection zone 35 is configured to have a sensitivity such that it is capable of detecting at least about 1 micromoles per liter of hydrogen peroxide, and in still other embodiments, 5 micromoles per liter of hydrogen peroxide. In certain embodiments, the second detection zone 35 is configured to have a sensitivity such that it is capable of detecting from at least about 1 micromole per liter to at least about 100 micromoles per liter of hydrogen peroxide.

The present invention provides a relatively simple, compact and cost-efficient device for accurately detecting D-lactic acid and/or hydrogen peroxide within a test sample (e.g., vaginal fluid). In this manner, for example, vaginal fluid may be tested in a single step for the biomarkers of good vaginal health. The test result may be visible so that it is readily observed by the person performing the test in a prompt manner and under test conditions conducive to highly reliable and consistent test results. In the event that the test indicates that vaginal health is less than optimum, the test can optionally provide steps that the woman can take to improve vaginal health. The device may then be discarded as a unit when the test is concluded. Such a single step detection technique has a variety of benefits. For example, as discussed above, a recurring test of vaginal health may help to prevent bacterial vaginosis or at least alert a woman to the onset of the same.

In accordance with the present disclosure, one or more of the devices described herein can be integrated into an absorbent article. An "absorbent article" generally refers to any article capable of absorbing fluids. Examples of some absorbent articles include, but are not limited to, disposable absorbent articles such as sanitary napkins, panty liners, adult incontinence garments, diapers, medical bandages and tampons such as those intended for medical use wherein a recurring test of vaginal health would be beneficial. As used herein, the phrase "absorbent article" generally refers to devices which absorb and contain body fluids, and more specifically, refers to devices which are placed against or near the skin to absorb and contain the various fluids discharged from the body. The term "disposable" is used herein to describe absorbent articles that are not intended to be laundered or otherwise restored or reused as an absorbent article after a single use.

Catamenial tampons suitable for use with the present invention are typically made of absorbent fibers, including natural and synthetic fibers, compressed into a unitary body of a size which may easily be inserted into the vaginal cavity. Suitable fibers include, for example, cellulosic fibers such as cotton and rayon. Fibers may be 100% cotton, 100% rayon, a blend of cotton and rayon, or other materials known to be suitable for tampon use.

Catamenial tampons are typically made in an elongated cylindrical form in order that they may have a sufficiently large body of material to provide the required absorbing capacity, but may be made in a variety of shapes. The tampon may or may not be compressed, although compressed types are now generally preferred. The tampon may be made of various fiber blends including both absorbent and nonabsorbent fibers, which may or may not have a suitable cover or wrapper. Suitable methods and materials for the production of tampons are well known to those skilled in the art.

Materials and processes suitable for forming the absorbent articles described herein are well known to those skilled in the art. Typically, absorbent articles include a substantially liquid-impermeable layer (e.g., outer cover), a liquid-permeable layer (e.g., bodyside liner, surge layer, etc.), and an absorbent core.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic kit for biomarkers of beneficial vaginal health comprising:
   a sample pad;
   a lateral chromatographic medium, the lateral chromatographic medium defining a first detection zone within which a D-lactic acid detection signal is capable of being generated, the D-lactic acid detection signal comprising a color change generated from a non-diffusively immobilized chromogen that is contained within the first detection zone, the D-lactic acid detection signal being generated in response to an enzyme-catalyzed reaction of D-lactic acid present in a sample, wherein the quantity of D-lactic acid present in the sample is determinable from the D-lactic acid detection signal, the chromatographic medium further defining a second detection zone within which a hydrogen peroxide detection signal is capable of being generated, the hydrogen peroxide detection signal comprising a color change generated from a non-diffusively immoblized chromogen that is contained within the second detection zone, wherein the presence or quantity of vaginal hydrogen peroxide present in a sample is determinable from the hydrogen peroxide detection signal, the lateral chromatographic medium providing for lateral flow from the sample pad through the first detection zone and through the second detection zone; and an absorbent material downstream of the lateral chromatograhic medium.

2. A diagnostic test kit as defined in claim 1, wherein the first detection zone comprises D-lactate dehydrogenase.

3. A diagnostic test kit as defined in claim 2, wherein the first detection zone further comprises diaphorase.

4. A diagnostic test kit as defined in claim 1, wherein the first detection zone comprises D-lactate oxidase.

5. A diagnostic test kit as defined in claim 1, wherein the first detection zone comprises a redox dye.

6. A diagnostic test kit as defined in claim 1, wherein the second detection zone comprises peroxidase.

7. A diagnostic test kit as defined in claim 1, wherein the second detection zone comprises redox dye.

8. A diagnostic test kit as defined in claim 1, wherein the diagnostic test kit is positioned in an absorbent article.

9. A method for detecting biomarkers of beneficial vaginal health comprising:
   i) contacting a test sample with the diagnostic kit of claim 1;
   ii) determining the presence or quantity of D-lactic acid from the D-lactic acid detection signal; and
   iii) determining the presence or quantity of vaginal hydrogen peroxide from the hydrogen peroxide detection signal.

10. A method as defined in claim 9, wherein the first detection zone comprises D-lactate dehydrogenase.

11. A method as defined in claim 10, wherein the first detection zone further comprises diaphorase.

12. A method as defined in claim 9, wherein the first detection zone comprises D-lactate oxidase.

\* \* \* \* \*